United States Patent

Da Re et al.

[11] Patent Number: 5,516,794
[45] Date of Patent: May 14, 1996

[54] XANTHONE DERIVATIVES, THEIR PREPARATION AND USE

[75] Inventors: Paolo Da Re; Giorgio Pifferi; Piero Valenti; Salvatore Malandrino, all of Milan, Italy

[73] Assignee: Inverni Della Beffa S.p.A., Milan, Italy

[21] Appl. No.: 399,852

[22] Filed: Mar. 7, 1995

Related U.S. Application Data

[63] Continuation-in-part of Ser. No. 115,239, Sep. 2, 1993, abandoned.

[30] Foreign Application Priority Data

Sep. 7, 1992 [IT] Italy .................. MI92A002071

[51] Int. Cl.⁶ .................. A61K 31/35; C07D 311/86
[52] U.S. Cl. .................. 514/455; 549/392
[58] Field of Search .................. 514/455; 549/392

[56] References Cited

PUBLICATIONS

Puranik et al., J. Org. Chem., 29(5), 1089–92 (1964).

*Primary Examiner*—Nicky Chan
*Attorney, Agent, or Firm*—Bucknam and Archer

[57] ABSTRACT

The novel compounds 3,6-Disubstituted xanthen-9-one of formula I

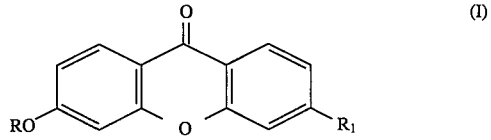

in which R is a $C_3$–$C_8$ linear, branched or cyclic alkyl and $R_1$ is linear, branched $C_1$–$C_8$ alkyl or cyclic $C_3$–$C_8$ alkyl or —OR in which R is as defined hereinabove, exhibit bone resorption inhibiting activity. Pharmaceutical compositions are described.

6 Claims, No Drawings

XANTHONE DERIVATIVES, THEIR PREPARATION AND USE

This application is a Continuation-in-part of U.S. Ser. No. 08/115,239 filed Sep. 2, 1993, now abandoned.

FIELD OF THE INVENTION

The present invention relates to new xanthone derivatives, to their synthesis and to their pharmacological use. More particularly, the invention refers to xanthen-9-one derivatives disubstituted at the positions 3 and 6, having the general formula

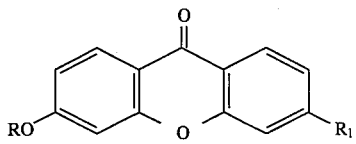

(I)

wherein R-$C_3$-$C_8$ linear, branched or cyclic alkyl and $R_1$=linear, branched $C_1$-$C_8$ alkyl or cyclic $C_3$-$C_8$ alkyl or an OR in which R is as defined hereinabove having bone resorption inhibiting activity.

BACKGROUND OF THE INVENTION

In the scientific literature, some synthetic xanthones having a remarkable interest in the pharmaceutical field, are reported. Among the most known compounds, reference is made to Mepixanox (P. Da Re et al., J. Med. Chem., 13, 527, 1970) active on the central nervous system as breath stimulant, xanthon-4-acetic acid having antitumor activity (G. W. Rawcastle et al., J. Med. Chem., 34, 2864, 1991) and a series of xanthon-2-carboxylic acids (AH7725, Xanoxic acid, Sudexanox) developed as anti-allergic (Drugs of the Future, 1, 313, 1976; ibidem, 1, 43, 1976; ibidem, 4, 736, 1979). Some xanthone derivatives of natural origin show different pharmacological properties, such as inhibition of monoaminooxidase, anti-inflammatory activity and antimicrobial activity (K. Hostettmann et al., Methods Plant Bioch., 1, 493, 1989). Puranik et al., J. Org. Chem. 29 (5) 1089–92 (1964) report the synthesis of 3-methoxy 6-methylxanthone but do not describe the biological properties of the substance.

SUMMARY OF THE INVENTION

It has now been surprisingly found that xanthones of formula I are endowed with bone resorption inhibiting activity so that they may be used as anti-osteoporosis agents.

The xanthones of the invention wherein $R_1$ is alkoxy have been prepared by alkylation of 3,6-dihydroxyxanthone II with suitable alkylating agents, according to the scheme:

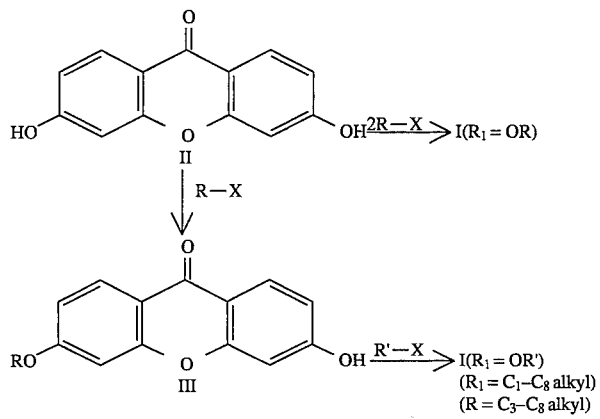

The starting compound, 3,6-dihydroxyanthone II may be prepared according to the method of P. K. Grover et al. (J. Chem. Soc. 3982, 1955).

The 3,6-dihydroxyanthone II is O-alkylated according to conventional etherification methods using as alkylating agent an alkyl halide (Example 1a and 1b) or an alkyl sulphate (Example 1c) in a polar solvent, such as, for instance, N,N-dimethylformamide, dimethylsulfoxide, acetone, or methylethylketone and performing the reaction in the presence of a base and at variable temperatures depending on the reactivity of the alkylating agent. The alkylated product is recovered from the reaction mixture and purified by crystallization from a suitable solvent.

The alkylation reaction may be accelerated when carried out in the presence of a phase-transfer catalyst. For instance the synthesis of I (R-iPr, $R_1$-OiPr) was carried out also in a two phase system consisting of toluene and water, in the presence of an excess of isopropylbromide and of sodium hydroxide and by catalysis with a quaternary ammonium salt, such as N-benzyltriethylammonium chloride.

The mixture is refluxed under stirring for 5 hours, cooled to room temperature and the reaction product is recovered from the organic phase by evaporating under vacuum and subsequent crystallization (Example 1a). Using only one mole of R-X halide it is possible to recover from the reaction mixture the monoether (Example 2a) which may then be further alkylated to give the 3,6-dialkoxy compounds I, symmetric and, with a different alkylating agent (R'-X), asymmetric ones (Example 2b).

The activity of the new xanthones has been evaluated in vitro and in vivo. The effect on the bone resorption has been studied in vitro according to Zambonin-Zallone et al. Anatomy Embriology, 165, 405, 1982). The medullary bone, deriving from tibia and femur of hens fed with hypocalcic diet for 7 days was washed with MEM buffer, modified according to Joklik, at 4° C. and filtered through a nylon filter with pore diameters of 112 microns. The obtained cell suspension was centrifuged at 1800 rpm for 5 minutes. The supernatant was discarded and the pellet treated with a 0.2% NaCl solution for 30 seconds to eliminate most of the present red blood cells. After restoration of the physiological osmolarity by means of 1.6% NaCl, the sample was centrifuged at 1800 rpm for 5 min. The obtained pellet, suspended again in the culture medium, was layered on 75% fetal calf serum in Joklik MEM for 45 min, so as to obtain a cell suspension enriched in osteoclasts. The fibroblasts were then filtered off by means of two filtrations on 112 un nylon filters.

The so obtained cells were cultivated in a nucleotide-free medium, in the presence of 3 µg/ml of cytosine-1-D-B-arabinofuranoside to block the mitosis of proliferating cells. The culture medium contained 100 µg/ml streptomycin, 100 U.I./ml penicillin and 10% fetal calf serum. The cultures were incubated in humid atmosphere saturated with 5% $CO_2$ at 37° C. and washed after 24 and 48 hours to remove non-adhering medullary cells.

The bone resorption was evaluated using the so prepared osteoclasts cultures cultured in the presence of rat bone particles, pre-labelled in vivo with trititated proline. During the resorption process, the collagen was degraded into fragments containing tritiated proline which was released in the culture medium; the resorption was calculated by measuring the radioactivity present in the medium after 24 and 48 hours of treatment.

Simultaneously to each experiment, cell-free samples have also been prepared containing only bone fragments labelled in the culture medium to measure the aspecific release of radioactivity from the bone. This value was subtracted as background from the corresponding experimental value.

The compounds under examination were added to the culture medium at the concentrations of 10 and 25 µg/ml dissolved in DMSO. The inhibiting effect on the bone resorption of osteoclast of compound I (R-iPr, $R_1$=OiPr), as an example, is reported on Table 1.

TABLE 1

Effect of the compound I (R = R' = OiPr) on bone resorption of hen osteoclasts

| Compound | Con. µg/ml | Bone Res. µg 24 h | 48 h | Inhibition % vs. controls 24 h | 48 h |
|---|---|---|---|---|---|
| Controls (DMSO) | — | 44.3 ± 7.5 | 72.7 ± 9.6 | — | — |
| I (R=iPr; $R_1$=OiPr) | 10 | 32.1 ± 3.6 | 50.2 ± 6.3 | 27.5 | 30.9 |
|  | 25 | 16.0 ± 1.0* | 21.0 ± 1.0* | 63.8 | 71.1 | n = 4 *p < 0.01

At the concentrations of 10 and 25 µg/ml, the compound showed a dose dependent activity. Particularly, the bone resorption inhibition was higher than 60% in comparison to unexposed controls, both at 24 and 48 hours.

The significance was evaluated by the Student's t test versus the group treated with the solvent alone (control).

In vivo, the antiosteoporotic activity of the compound I (R-iPr, $R_1$=OiPr) administered by the oral route, was evaluated on suckling rats under low calcium diet according to the method, slightly modified, disclosed by Lozupone et al., Bone, 9; 215, 1988). Female Wistar rats were allowed to delivery spontaneously.

The offsprings were pooled, weighed and redistributed so as to obtain nests similar in weight and number.

The mothers during the suckling period were fed with a low calcium diet (Altromin DP 1031) and divided in two groups.

One group was treated orally with compound I (R-iPr, $R_1$=OiPr) suspended in Methocel 0.5% at the dose of 250 mg/kg, whereas the second was treated with the vehicle alone (control group). The animals were sacrificed after 10 days from the start of milking.

The femur was taken from each animal and fixed, included in methacrylate and transversally cut. Two sections taken at the distal methaphysis and one from the medial methaphysis were microradiographed so as to measure the thickness of the compacta.

The results are reported in Table 2.

TABLE 2

| Compound | Dose mg/kg/os | Compacta thinkness | | | |
|---|---|---|---|---|---|
| | | Diaphysis mm ± S.D. | % | Methaphysis mm ± S.D. | % |
| Control (Methocel 0.5%) | — | 0.55 ± 0.04 | — | 0.31 ± 0.08 | — |
| I (R=iPr; $R_1$=OiPr) | 250 | 0.71 ± 0.03* | +29 | 0.40 ± 0.12* | +29 | n = 3 *p < 0.05

The compound under examination shows a significant antiosteoporotic activity, the thickness being 29% higher than in the control group both in the diaphysis and in the methaphysis.

The acute toxicity of the compound I (R-iPr; $R_1$= OiPr) was evaluated in the rat after oral and intraperitoneal administration.

Sprague-Dawley rats of both sexes (5M+5 F) were used for each group. After treatment, the animals were observed for 14 days and the $LD_{50}$ was calculated with the probit methods (Finney D. J. in "Probit Analysis", Cambridge University Press, $3^d$ Ed., Cambridge, 1971). The compound has an $LD_{50}$>4000 mg/kg ($LD_0$) after oral administration and an $LD_{50}$>1000 mg/kg ($LD_{20}$) by intraperitoneal route.

The significant bone resorption inhibiting activity and the low acute toxicity make the compounds of the invention particularly suitable as antiosteoporotic agents in man.

EXAMPLE 1 a) 3,6-Di(isopropoxy)xanthone (I, R-iPr, $R_1$=OiPr) A mixture of 27.5 g (0.121 mol) of 3,6-dihydroxy-xanthone (II), 54.6 ml (0.546 mol) of isopropylbromide and 27.5 g of N-benzyltriethylammonium chloride in 1 l toluene and 580 ml of 50% aqueous sodium hydroxide was refluxed under stirring for 5 hours. The mixture was cooled to room temperature and the organic phase was separated, washed with water to neutrality, dried on sodium sulphate and evaporated. The residue was crystallized from ligroine to yield 31 g (84%) of I (R-iPr, $R_1$=OiPr) m.p. 135° C. ($M^+$ at m/z 312).

b) 3,6-Di(cyclopentyloxy)xanthone (I, R-$C_5H_9$, $R_1$=O$C_5H_9$) 1.2 g (0.005 mol) of dihydroxyxanthone (II), 2 g of anhydrous potassium carbonate and 2 ml (0.019 mol) of cyclopentylbromide in 60 ml of dimethylformamide were refluxed under stirring for 14 hours. The dimethylformamide was evaporated and the residue was dissolved in water and methylene chloride, which was separated, washed with water, dried on sodium sulphate and evaporated. The residue was crystallized from ligroine to give 1.2 g (63%) of I (R=$C_5H_9$, $R_1$-O$C_5H_9$), m.p. 143°– 145° C. ($M^+$ at m/z 364).

c) 3,6-Di(n-butoxy)xanthone (I, R=n-Bu, $R_1$=n-BuO 500 mg of anhydrous potassium carbonate and 550 mg (2.6 mmol) of di-n-butylsulfate were added to a solution of 300 mg (1.3 mmol) of dihydroxyxanthone (II) in 20 ml of dimethylformamide and the mixture was refluxed under stirring for 7 hours. The mixture was poured into water, filtered, washed and dried. 200 mg (45%) of I (R=n-Bu, $R_1$-n-BuO) were obtained after crystallization from ligroin, m.p. 84°–86° C. ($M^+$ at m/z 340).

EXAMPLE 2 a) 3-Isopropoxy-6-hydroxyxanthone (III, R-iPr) 1 g (0.005 mol) of dihydroxyxanthone (II) were suspended in 50 ml of toluene, 1 g of N-benzyltriethylammonium chloride and 0.5 ml (0.005 mmol) of isopropyl bromide were added and then 25 ml of 50% NaOH. The mixture was refluxed under stirring for 6 hours and the phases were separated: the toluene phase gave after evaporation 0.28 g of 3,6-diisopropoxyxanthone. The aqueous phase was acidified and the solid was filtered and dried. Recrystallization from toluene afforded 0.26 g of product (III, R=iPr), m.p. 268°–281° C. ($M^+$ at m/z 270).

b) 3-Isopropoxy-6-n-propoxy-xanthone (I, R-iPr, $R_1$-OPr) 0.16 g of the previous compound (III, R-iPr), 0.2 g of anhydrous $K_2CO_3$ and 0.1 ml of iodopropane in 20 ml of acetone were refluxed under stirring for 9 hours. The mixture was filtered at high temperature, washed with acetone and evaporated. The residue crystallized from ligroin gave 100 mg of product having m.p. 78°–80° C. ($M^+$ at m/z 312).

EXAMPLE 3 a) 2-(3-Methylphenoxy)-4-fluorobenzoic acid (V, Hal-F, $R_1$=Me) A mixture of 3.8 g (0.014 mol) of 2-iodo-4-fluorobenzoic acid (IV, Hal(2)-J, Hal(4)-F), 1.5 ml (0.014 mol) of m-cresol, 3.5 g of anhydrous $K_2CO_3$, 0.5 g of copper powder and 0.5 g of CuI in 40 ml of nitrobenzene were heated 170°–180° C. for 8 hours under stirring. The nitrobenzene was steam distilled and the mixture was filtered and acidified with diluted HCl. After filtration and washing with water, the residue was dissolved in aqueous bicarbonate and acidified again with diluted HCl. The product was filtered, washed and dried to give 1.8 g (52% yield) of V (Hal-F, $R_1$=Me), m.p. 110°–112° C. ($M^+$ at m/z 246).

b) 3-Methyl-6-fluoroxanthone (VI, Hal-F, $R_1$=Me) 20 g of phosphoric anhydride and then 1.8 g of the previous compound (V, Hal-F, $R_1$=Me) were added to 20 ml of 85% phosphoric acid and the mixture was heated to 120° C. under stirring for 5 hours. The reaction mixture was then poured into ice, filtered, washed with water and dried: about 2 g of a mixture of 1-methyl-6-fluoroxanthone and of 3-methyl-6-fluoroxanthone were obtained which was chromatographed on silica gel. 6.8 g of the impurity 1-methyl-6-fluoroxanthone and 0.7 g of 3-methyl-6-fluoro-xanthone (VI, Hal-F, $R_1$=Me), m.p. 161°–162° C. ($M^+$ at m/z 228) were recovered.

c) 3-Methyl-6-cyclopentyloxyxanthone (I, R=$C_5H_9$, $R_1$=Me) A solution of 1 g of sodium metal in 30 ml of cyclopentanol was prepared. 1 g of the previous 3-methyl-6-fluoroxanthone (VI, Hal-F, $R_1$=Me) was separately dissolved in 30 ml of dioxane. The two solutions were mixed and refluxed for 100 hours. The mixture was evaporated, the residue was dissolved with diluted HCl and stirred for 1 hour. After extraction with methylene chloride, the mixture was washed with diluted HCl and then with water, dried on sodium sulphate and evaporated. The residue was chromatographed on silica gel eluting with petroleum ether:ethyl acetate 9:1 and crystallized from ligroine to give 0.22 g of I (R-$C_5H_9$, $R_1$-Me), m.p. 105°–106° C. ($M^+$ at m/z 294).

d) 3-Methyl-6-isopropoxyxanthone (I, R-iPr, $R_1$= Me) A solution of 330 mg (1.45 mmol) of 3-methyl-6-fluoroxanthone (VI, Hal-F, $R_1$=Me) in 10 ml of isopropanol was added to a solution of 740 mg of KOH in 10 ml of isopropanol. 4.2 g of tetrabutylammonium bromide were then added and the mixture was heated to 75° C. for 6 hours under stirring. The isopropanol was evaporated, the residue dissolved with diluted HCl and extracted with $CH_2Cl_2$. The organic phase was evaporated, washed with diluted HCl, then with water, dried and evaporated. The residue was chromatographed on silica gel eluting with toluene. The isolated product crystallized from ligroine gave 100 mg (26%) of I (R-iPr, $R_1$=Me), m.p. 94°–96° C. ($M^+$ at m/z 268).

EXAMPLE 4 a) 2-(3-Methylphenoxy)-4-chlorobenzoic acid (V, Hal-Cl, $R_1$-Me) A mixture of 57.3 g (0.3 mol) of 2,4-dichlorobenzoic acid (VI, Hal-Cl, $R_1$, =Me), 32.4 g (0.3 mol) of m-cresol, 100 g of anhydrous potassium carbonate, 2 g of copper powder and 2 g of CuI in 500 ml of nitrobenzene was refluxed at 170°–180° C. for 6 hours under stirring. The nitrobenzene was steam distilled, filtered and acidified with diluted HCl. The mixture was filtered, washed, dried, extracted with hot ligroine, from which the product crystallized. 52 g of product V were obtained (66% yield) ($R_1$=Me, Hal-Cl) having m.p. 153°–155° C. ($M^+$ at m/z 262).

b) 3-Methyl-6-chloroxanthone (VI, Hal-Cl, $R_1$=Me) 500 g of phosphoric anhydride and then 50 g of the previous product (V, Hal-Cl, $R_1$=Me) were added to 500 ml of 85% phosphoric acid; the mixture was stirred at 100° C. for 3 hours. The mixture was poured into ice, filtered, washed with water and dried: about 40 g of a mixture of 1-methyl-6-chloroxanthone and of 3-methyl-6-chloroxanthone was obtained. 20 g of the previous mixture were chromatographed on silica gel column. The impurity 1-methyl-6-chloroxanthone (7 g, m.p. 111°–113° C.) was first isolated and then 7.5 g of 3-methyl-6-chloroxanthone (VI, Hal-Cl, $R_1$=Me) having m.p. 144°–147° C. ($M^+$ at m/z 244).

c) 3-Methyl-6-isopropoxyxanthone (I, R-iPr, $R_1$=Me) A solution of 350 mg (1.43 mmol) of 3-methyl-6-chloroxanthone (VI, Hal-Cl, $R_1$=Me) in 10 ml of isopropanol was added to a solution of 740 mg of KOH in 10 ml of isopropanol. 4.2 g of tetrabutylammonium bromide were then added and the mixture was then stirred at 75° C. for 6 hours. The solvent was evaporated, the residue was dissolved in diluted HCl and extracted with $CH_2Cl_2$. The organic phase was evaporated, washed with diluted HCl, then with water, dried and evaporated. The residue was chromatographed on silica gel eluting with toluene. The isolated product was crystallized from ligroine to give 80 mg (21%) of I (R-iPr, $R_1$=Me), m.p. 94°–96° C. ($M^+$ at m/z 268).

The compounds of the invention may be administered orally to humans in an amount of 50–1000 mgs, preferably 100–500 mgs 1–3 times a day, depending on the weight, the age and the condition of the patient. Pharmaceutical compositions also contain pharmaceutically acceptable excipients which are inert to the active ingredient, such as maize starch, potato starch, rice starch, modified starch, lactose, cellulose, methyl cellulose, hydroxypropyl cellulose, sodium carboxymethyl cellulose, microcrystalline cellulose, silica gel powder, magnesium stearate, talc, povidone, crosspovidone, sodium lauryl sulfate, aqueous and oily vehicles and emulsifying agents. The compositions may be in the form of solutions, emulsions, capsules and tablets.

Examples 5 and 6 hereinbelow illustrate two tablets containing as the active ingredients 3,6-(diisopropoxy)xanthone.

EXAMPLE 5

Each tablet contains:

| | |
|---|---|
| 3,6-di(isopropoxy)xanthone | 50 mg |
| Maize starch | 60 mg |
| lactose | 15 mg |
| Methylcellulose | 2 mg |
| Microcrystalline cellulose | 77 mg |
| Silica gel powder | 16 mg |
| Magnesium stearate | 3 mg |
| Sodium carboxymethylcellulose | 15 mg |
| Talc | 10 mg |

EXAMPLE 6

Each tablet contains:

| | |
|---|---|
| 3,6-di(isopropoxy)xanthone | 200 mg |
| Microcrystalline cellulose | 90 mg |
| Modified starch | 20 mg |
| Povidone | 16 mg |
| Crospovidone | 14 mg |
| Magnesium stearate | 6 mg |
| Silica gel powder | 3 mg |
| Sodium lauryl sulfate | 1 mg |

What is claimed is:

1. A 3,6-Disubstituted xanthen-9-one of formula I

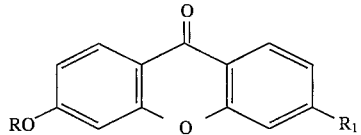

wherein R is a $C_3$–$C_8$ linear, branched or cyclic alkyl and $R_1$ is linear, branched $C_1$–$C_8$ alkyl or cyclic $C_3$–$C_8$ alkyl or —OR in which R is as defined hereinabove.

2. A compound according to claim 1, which is a) 3,6-di(isopropoxy)xanthone, b) 3,6-di(n-butoxy)xanthone, c) 3,6-di(cyclopentyloxy)xanthone, d) 3-isopropoxy-6-n-propoxy-xanthone, e) 3-methyl 6-isopropoxyxanthone or f) 3-methyl 6-cyclopentyloxyxanthone.

3. A pharmaceutical composition for the treatment of a living subject affected by bone resorption containing as the active ingredient a 3,6-Disubstituted xanthen-9-one of formula I

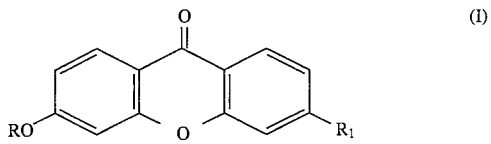

according to claim 1 in unit dose form containing 50–1000 mgs per dose and pharmaceutically acceptable excipients.

4. The composition according to claim 3 in the form of a solution, an emulsion, a capsule or a tablet.

5. A method of treatment of a living subject affected by bone resorption which consists of administering orally an effective amount of a 3,6-Disubstituted xanthen-9-one of formula I

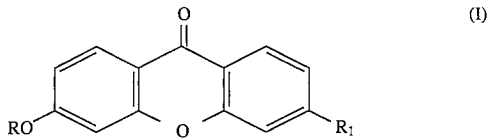

wherein R is a $C_3$–$C_8$ linear branched or cyclic alkyl and $R_1$ is linear, branched $C_1$–$C_8$ alkyl or cyclic $C_3$–$C_8$ alkyl or —OR in which R is as defined hereinabove.

6. The method according to claim 5 wherein a composition containing 50–1000 mgs of said compound per unit dose is administered 1–3 times a day.

* * * * *